United States Patent
Oldham et al.

(10) Patent No.: US 6,965,105 B2
(45) Date of Patent: *Nov. 15, 2005

(54) SCANNING SYSTEM AND METHOD FOR SCANNING A PLURALITY OF SAMPLES

(75) Inventors: Mark F. Oldham, Los Gatos, CA (US); Eugene F. Young, Marietta, GA (US)

(73) Assignee: Applera Corporation, Foster City, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/387,755

(22) Filed: Mar. 13, 2003

(65) Prior Publication Data

US 2003/0133108 A1 Jul. 17, 2003

Related U.S. Application Data

(63) Continuation of application No. 09/617,549, filed on Jul. 14, 2000, now Pat. No. 6,563,581.

(51) Int. Cl.[7] ............ H01J 3/14; H01J 40/14; H01J 5/16; G01N 21/64
(52) U.S. Cl. .............. 250/236; 356/317; 356/417; 250/458.1; 250/459.1; 250/456.1; 250/456.2
(58) Field of Search .......... 250/236, 458.1, 250/459.1, 456.1, 456.2, 461.1; 356/317, 417, 246, 318; 359/216, 209, 210, 317; 422/82.08, 942; 436/172

(56) References Cited

U.S. PATENT DOCUMENTS

| | | |
|---|---|---|
| 3,060,319 A | 10/1962 | Greunke |
| 3,544,190 A | 12/1970 | Moorhusen et al. |
| 3,773,426 A | 11/1973 | Mudd |
| 3,909,103 A | 9/1975 | Graves et al. |

(Continued)

FOREIGN PATENT DOCUMENTS

| | | |
|---|---|---|
| CH | 556 591 | 10/1973 |
| DE | 197 48 211 A1 | 5/1999 |
| EP | 0 767 373 A2 | 4/1997 |
| EP | 0 981 043 A1 | 2/2000 |
| JP | 2001-83090 A | 3/2001 |
| WO | WO 97/36681 A1 | 10/1997 |
| WO | WO 97/46707 A2 | 12/1997 |
| WO | WO 97/46712 A3 | 12/1997 |
| WO | WO 97/46712 | 12/1997 |
| WO | WO 00/25922 A2 | 5/2000 |
| WO | WO 01/27635 A1 | 4/2001 |
| WO | WO 01/35079 A1 | 5/2001 |
| WO | WO 02/06796 A2 | 7/2001 |

OTHER PUBLICATIONS

Partial International Search for Application No. PCT/US2004/005012 dated Jul. 20, 2004.

(Continued)

Primary Examiner—John R. Lee
Assistant Examiner—Kalimah Fernandez

(57) ABSTRACT

A system for detecting fluorescence emitted from a plurality of samples in a sample tray is provided. The system generally includes a plurality of lenses positioned in a linear arrangement, a linear actuator configured to translate the plurality of lenses, an excitation light source for generating an excitation light, an excitation light direction mechanism for directing the excitation light to a single lens of the plurality of lenses at a time so that a single sample holder aligned with the lens is illuminated at a time, and an optical detection system for analyzing light from the sample holders. In certain embodiments, the optical detection system includes a light dispersing element configured to spectrally disperse the light from the sample holder being illuminated, and a lens element configured to receive light from the light dispersing element and direct the light onto a light detection device. A method of scanning a sample tray having a plurality of samples positioned in sample holders to detect fluorescence is also provided.

19 Claims, 8 Drawing Sheets

U.S. PATENT DOCUMENTS

| | | | |
|---|---|---|---|
| 3,970,359 A | | 7/1976 | Starkweather |
| 4,004,150 A | | 1/1977 | Natelson |
| 4,050,780 A | | 9/1977 | Wei et al. |
| 4,115,010 A | | 9/1978 | McAleer et al. |
| 4,378,480 A | * | 3/1983 | Langhans ................ 219/121.7 |
| 4,498,780 A | * | 2/1985 | Banno et al. ............... 356/414 |
| 4,626,684 A | * | 12/1986 | Landa ........................ 250/328 |
| 4,640,573 A | | 2/1987 | Kataoka et al. |
| 4,668,080 A | * | 5/1987 | Gale et al. ..................... 355/51 |
| 4,762,420 A | * | 8/1988 | Bowley ....................... 356/436 |
| 4,874,920 A | * | 10/1989 | Yamazaki et al. ..... 219/121.85 |
| 4,950,862 A | * | 8/1990 | Kajikawa ............... 219/121.68 |
| 4,970,546 A | * | 11/1990 | Suzuki et al. ................. 355/53 |
| 4,999,511 A | * | 3/1991 | Kohno .................. 250/559.11 |
| 5,014,707 A | | 5/1991 | Schwarz et al. |
| 5,130,838 A | | 7/1992 | Tanaka et al. |
| 5,153,437 A | | 10/1992 | Nishii et al. |
| 5,166,800 A | * | 11/1992 | Mori et al. .................. 348/303 |
| 5,169,601 A | | 12/1992 | Ohta et al. |
| 5,309,273 A | | 5/1994 | Mori et al. |
| 5,355,215 A | | 10/1994 | Schroeder et al. |
| 5,397,709 A | | 3/1995 | Berndt |
| 5,424,841 A | | 6/1995 | Van Gelder et al. |
| 5,459,325 A | | 10/1995 | Hueton et al. |
| 5,504,612 A | | 4/1996 | Cobb et al. |
| 5,557,398 A | * | 9/1996 | Wechsler et al. ........... 356/318 |
| 5,583,686 A | | 12/1996 | Chen |
| 5,589,136 A | | 12/1996 | Northrup et al. |
| 5,589,351 A | | 12/1996 | Harootunian |
| 5,657,118 A | | 8/1997 | Lee |
| 5,659,420 A | * | 8/1997 | Wakai et al. ................ 359/368 |
| 5,721,435 A | | 2/1998 | Troll |
| 5,784,152 A | | 7/1998 | Heffelfinger et al. |
| 5,789,173 A | | 8/1998 | Peck et al. |
| 5,822,060 A | | 10/1998 | Linowski et al. |
| 5,854,803 A | * | 12/1998 | Yamazaki et al. ............. 372/31 |
| 5,910,287 A | | 6/1999 | Cassin et al. |
| 5,922,285 A | | 7/1999 | Melendez et al. |
| 5,928,907 A | | 7/1999 | Woudenberg et al. |
| 5,936,730 A | | 8/1999 | Foley et al. |
| 5,942,432 A | | 8/1999 | Smith et al. |
| 6,024,920 A | | 2/2000 | Cunanan |
| 6,043,506 A | | 3/2000 | Heffelfinger et al. |
| 6,043,880 A | | 3/2000 | Andrews et al. |
| 6,133,986 A | * | 10/2000 | Johnson ....................... 355/67 |
| 6,185,030 B1 | | 2/2001 | Overbeck |
| 6,201,639 B1 | | 3/2001 | Overbeck |
| 6,210,996 B1 | * | 4/2001 | Yamazaki et al. .......... 438/150 |
| 6,211,989 B1 | * | 4/2001 | Wulf et al. ................. 359/210 |
| 6,252,664 B1 | | 6/2001 | Barbera-Guillem |
| 6,310,687 B1 | * | 10/2001 | Stumbo et al. ............. 356/317 |
| 6,341,118 B1 | | 1/2002 | Drobot et al. |
| 6,355,934 B1 | | 3/2002 | Osgood et al. |
| 6,369,893 B1 | | 4/2002 | Christel et al. |
| 6,399,952 B1 | | 6/2002 | Maher et al. |
| 6,472,156 B1 | | 10/2002 | Wittwer et al. |
| 6,490,533 B2 | | 12/2002 | Weiner et al. |
| 6,519,032 B1 | * | 2/2003 | Kuebler et al. ............. 356/337 |
| 6,521,181 B1 | | 2/2003 | Northrup et al. |
| 6,524,532 B1 | | 2/2003 | Northrup |
| 6,563,581 B1 | * | 5/2003 | Oldham et al. ............. 356/317 |
| 6,563,584 B1 | * | 5/2003 | Yurino et al. ............... 356/417 |
| 6,565,815 B1 | | 5/2003 | Chang et al. |
| 6,586,750 B2 | | 7/2003 | Montagu et al. |
| 6,587,277 B2 | * | 7/2003 | Yamazaki et al. .......... 359/623 |
| 6,602,473 B1 | | 8/2003 | Northrup |
| 6,620,623 B1 | * | 9/2003 | Yershov et al. ............. 436/172 |
| 6,770,546 B2 | * | 8/2004 | Yamazaki .................... 438/487 |
| 6,816,231 B2 | * | 11/2004 | Tsujikawa et al. ............. 355/53 |
| 2002/0074512 A1 | | 6/2002 | Montagu et al. |
| 2002/0109844 A1 | | 8/2002 | Christel et al. |
| 2002/0159057 A1 | | 10/2002 | Odoy et al. |
| 2002/0159058 A1 | | 10/2002 | Weiner |
| 2002/0161529 A1 | | 10/2002 | Weiner et al. |

OTHER PUBLICATIONS

International Search Report for PCT/US01/41350 dated Apr. 8, 2002.

Nie, Shuming and Zare, Richard, "Optical Detection of Single Molecules." *Annual Review of Biophysical Biomolecular Structure* 26:567–96 (1997).

International Search Report for International Application No. PCT/US2004/005012 dated Nov. 4, 2004.

* cited by examiner

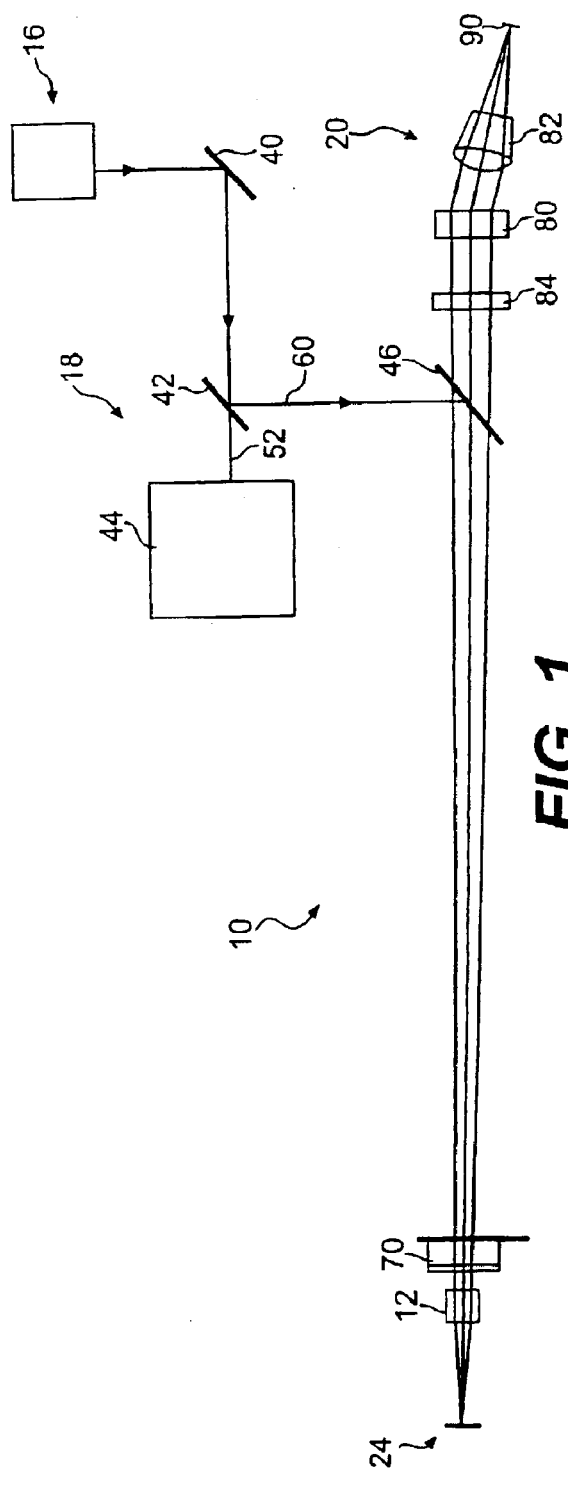
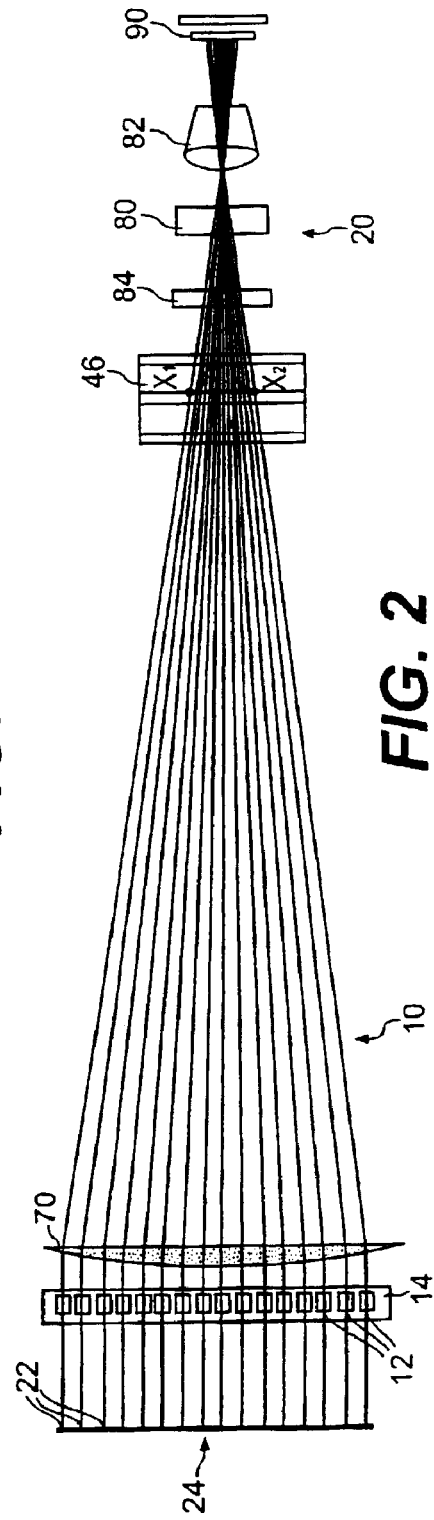
FIG. 1
FIG. 2

SCANNING SYSTEM AND METHOD FOR SCANNING A PLURALITY OF SAMPLES

CROSS REFERENCE TO RELATED APPLICATIONS

This application is a continuation of application Ser. No. 09/617,549 filed Jul. 14, 2000 now U.S. Pat. No. 6,563,581.

FIELD OF THE INVENTION

This invention relates to systems and methods for scanning a sample tray with a plurality of samples. The invention further relates to detection systems for detecting fluorescence from a plurality of samples in a sample tray.

BACKGROUND

Biological testing involving analyzing the chemical composition of nucleic acid samples in order to determine the nucleotide sequence of the sample has become increasingly popular. Currently, experiments in chemistry and biology typically involve evaluating large numbers of samples using techniques such as detection of fluorescence emitted from a sample in conjunction with a polymerase chain reaction (PCR). These experiments, as well as other techniques such as sequencing of nucleic acid samples, are typically time consuming and labor intensive. Therefore, it is desirable that a large number of samples can be analyzed quickly and accurately. With large scale projects such as the Human Genome Project, it is desirable to increase throughput of nucleic acid sequencing and polymerase chain reactions.

Existing systems are typically not well-adapted for real-time detection of a plurality of samples in an efficient manner. Existing systems typically include a separate detector for each sample well and are not compatible for large-scale testing using fluorescent detection. Therefore, there is a need for an efficient method and system for real-time detection of a plurality of sample wells of a sample well tray.

SUMMARY OF THE INVENTION

The advantages and purposes of the invention will be set forth in part in the description which follows, and in part will be obvious from the description, or may be learned by practice of the invention. The advantages and purposes of the invention will be realized and attained by the elements and combinations particularly pointed out in the appended claims.

To attain the advantages and in accordance with the purposes of the invention, as embodied and broadly described herein, the invention includes a scanning system for detecting fluorescence emitted from a plurality of samples in a sample tray. According to certain embodiments of the invention, the optical system generally includes a plurality of lenses positioned in a linear arrangement, an excitation light source for generating an excitation light, an excitation light direction mechanism for directing the excitation light to a single lens of the plurality of lenses at a time so that a single sample holder aligned with the lens is illuminated at a time, and an optical detection system for analyzing light from the sample holders. The plurality of lenses and sample tray are configured so that relative motion may be imparted between the plurality of lenses and the sample well tray so that the plurality of lenses may linearly translate in a second direction perpendicular to a first direction of the linear row of sample holders. Preferably, the excitation light source directs the excitation light to each of the sample holders of a row of sample holders in a sequential manner as the plurality of lenses linearly translates in the second direction. A sample in the sample holder may generate light, e.g. fluoresce, upon illumination. In certain embodiments, the optical detection system includes a light dispersing element configured to spectrally disperse the light from the sample holder being illuminated, and a lens element configured to receive light from the light dispersing element and direct the light onto a light detection device. In certain embodiments, the sample holders are sample wells.

In another aspect of the present invention, the invention is directed toward a detection system for detecting fluorescence from a plurality of sample holders in a sample tray. In certain embodiments, the detection system includes a single excitation source for generating an excitation light, a lens housing comprising a plurality of lenses positioned in a linear row, each lens configured to direct the excitation light source to an aligned sample holder, and a single detection device for analyzing light from the plurality of sample holders. The linear row of lenses is arranged to be angularly offset relative to an adjacent row of sample holders.

In yet another aspect of the present invention, the invention includes a method of scanning a sample tray having a plurality of samples positioned in sample holders to detect fluorescence. The method includes generating an excitation light with an excitation light source, directing the excitation light to a first lens of a row of lenses, the row of lenses being angularly offset relative to an adjacent row of sample holders, illuminating a sample in a first sample holder of the row of sample holders positioned adjacent the row of lenses with the excitation light to generate an emission light, optically detecting the optical characteristics of the emission light, directing the excitation light to a second lens positioned adjacent the first lens of the row of lenses, illuminating a sample in a second sample holder of the row of sample holders to generate an emission light, and optically detecting the optical characteristics of the emission light from the second sample holder. Throughout the above method of scanning, relative motion is imparted between the row of lenses and the sample tray so that the row of lenses is linearly translated in a direction perpendicular to the row of sample wells.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain principles of the invention. In the drawings, FIG. 1 is a front schematic view of a system for scanning a plurality of sample wells and measuring the fluorescence of the samples therein according to certain embodiments of the present invention;

FIG. 2 is a side schematic view of the system of FIG. 1;

DESCRIPTION OF PREFERRED EMBODIMENTS

Figure 3:
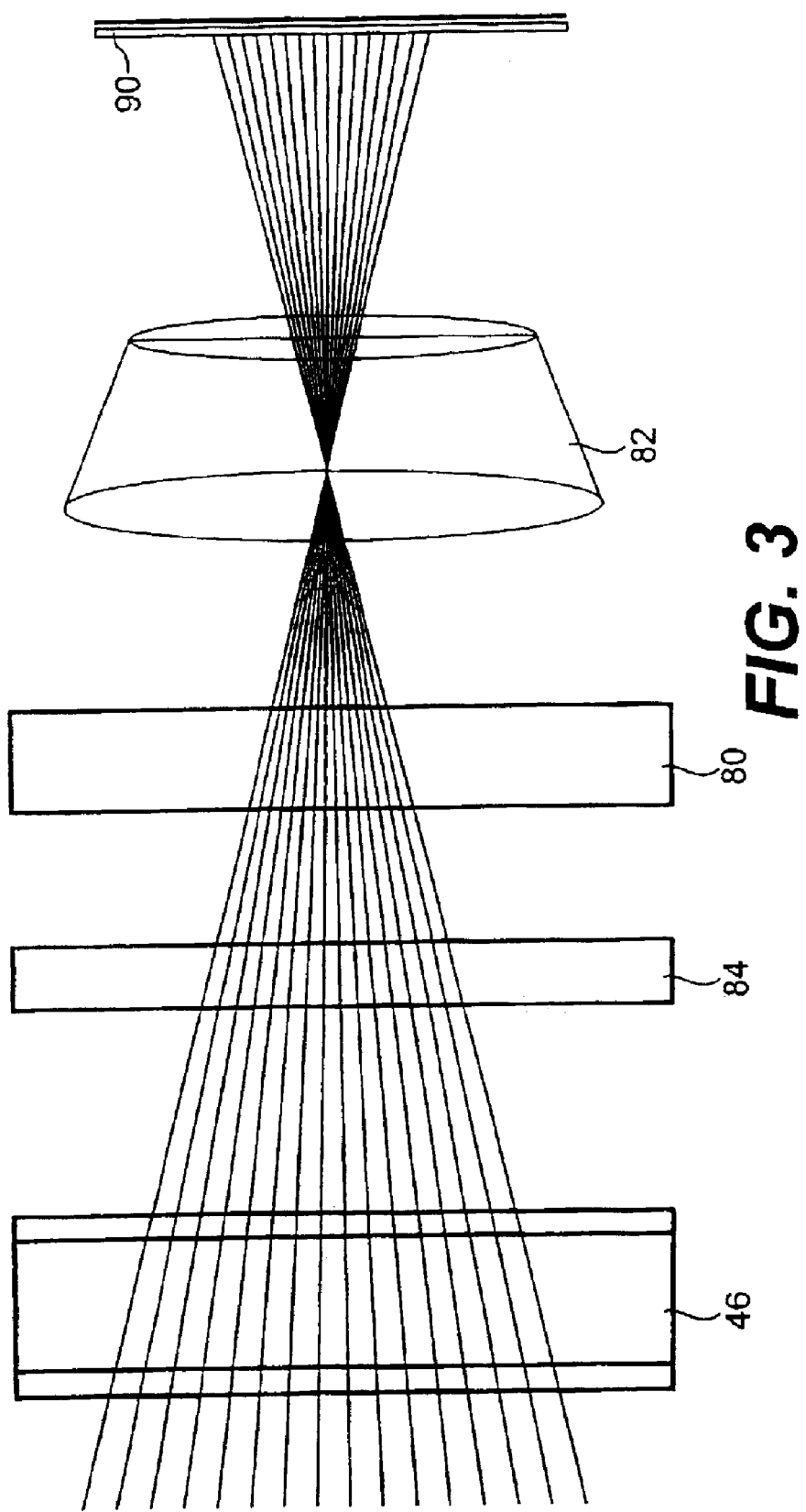
FIG. 3 is a close up side schematic view of a portion of an optical system.
Figure 4:
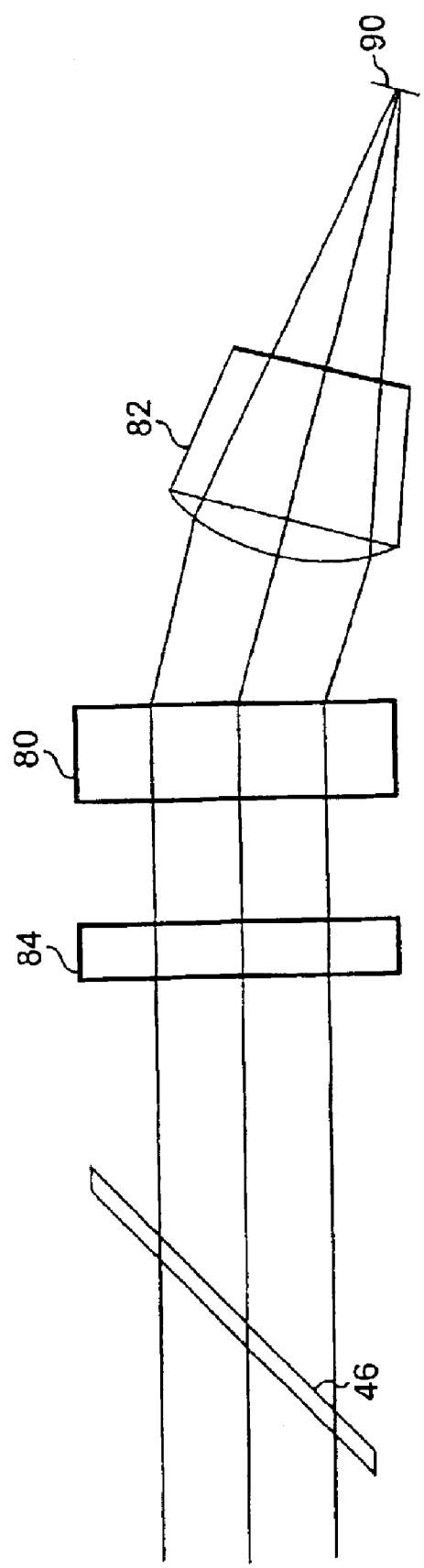
FIG. 4 is a close up front schematic view of a portion of an optical system.

Reference will now be made in detail to several preferred embodiments of the invention, examples of which are illustrated in the accompanying drawings. Wherever possible, the same reference numbers will be used throughout the drawings to refer to the same or like parts.

According to certain embodiments, the present invention provides a scanning system for detecting fluorescence emitted from a plurality of samples in a sample tray. According to certain embodiments of the invention, the optical system generally includes a plurality of lenses positioned in a linear arrangement, an excitation light source for generating an excitation light, an excitation light direction mechanism for directing the excitation light to a single lens of the plurality of lenses at a time so that a single sample well aligned with the well lens is illuminated at a time, and an optical detection system for analyzing light from the sample holders. Preferably, the excitation light source directs the excitation light to each of the sample holders of a row of sample holders in a sequential manner as the plurality of lenses linearly translates in a first direction relative to the sample tray, the sample holder generating light upon illumination. Either the plurality of lenses or the sample tray may be translated so that a relative motion is imparted between the plurality of lenses and the sample tray.

The present invention further provides methods of scanning a sample well tray, which has a plurality of samples positioned in sample holders, to detect fluorescence. The method includes generating an excitation light with an excitation light source, and directing the excitation light to a first lens of a row of lenses, the row of lenses being angularly offset relative to an adjacent row of sample holders. The method further includes illuminating a sample in a first sample holder of the row of sample holders positioned adjacent the row of lenses with the excitation light to generate an emission light, and optically detecting the spectral characteristics of the emission light. Preferably, the method includes directing the excitation light to a second lens positioned adjacent the first lens of the row of lenses, illuminating a sample in a second sample holder of the row of sample holders to generate an emission light, and optically detecting the spectral characteristics of the emission light from the second sample holder. In certain embodiments, the row of lenses is linearly translated in a direction substantially perpendicular to the row of sample holders throughout the above methods. In other embodiments, the row of sample holders is linearly translated relative to the row of lenses. In certain embodiments, the sample holders are sample wells.

According to certain embodiments shown in FIGS. 1–7, the scanning system 10 for detecting fluorescence includes a plurality of well lenses 12 positioned in a well lens housing 14, an excitation light source 16, an excitation light direction mechanism 18 for directing the excitation light to a single well lens at a time, and an optical detection system 20 for analyzing light from the sample wells 22 of the sample well tray 24 or other sample holding device.

In accordance with certain embodiments of the present invention, the scanning system includes a plurality of lenses, hereinafter referred to as well lenses, positioned in a linear arrangement. As embodied herein and shown in FIGS. 1–5, the plurality of well lens 12 are positioned within a well lens housing 14. In certain preferred embodiments, the well housing contains a single row of well lenses 12 arranged so that the well lenses are equally spaced from each other, as shown in FIG. 2. The well lenses 12 are arranged in a linear manner within the well housing. The well lens are arranged so that each of the well lenses will align with a corresponding column of sample wells in a sequential manner as the well lens housing is linearly translated relative to an adjacent sample well tray. Throughout the scanning of the sample well tray, the well lens housing moves at a substantially uniform speed relative to the sample well tray in a plane parallel to the top surface of the sample well tray. For example, the well lens housing 14 in FIG. 2 moves in a first direction (into the page in FIG. 2) as the well lens housing 14 linearly translates in a plane parallel to the top surface of sample well tray 24. In other embodiments, the sample well tray is linearly translated relative to a stationary well lens housing.

The well lens housing is preferably positioned adjacent a sample well tray with a plurality of sample wells to be scanned. As shown in FIG. 2, the well lens housing is preferably positioned adjacent a stationary sample well tray 24 with a plurality of sample wells 22. In certain embodiments, the sample well tray 24 has a number of columns equal to the number of well lenses in the well lens housing. In the example shown, the sample well tray is 384-well tray. In a 384-well sample well tray, the wells are arranged in a sixteen by twenty-four array with sixteen columns and twenty-four rows. The scanning device is also preferably configured for use with 96-well sample trays, in addition to microcard sample trays.

Examples of sample well trays suitable for use in the apparatus of the present invention are described in PCT Application No. WO#00/25922 to Moring et al., which is assigned to the assignee of the present invention, the contents of which are hereby incorporated by reference herein for any purpose. Examples of microcard sample trays suitable for use in the apparatus of the present invention are described in PCT Application No. WO#97/36681 to Woudenberg et al., which is assigned to the assignee of the present invention, the contents of which are hereby incorporated by reference herein for any purpose. Sample well trays having any number of sample wells and sample well sizes may also be used. According to certain embodiments, the volume of the sample wells may vary anywhere from 0.01 $\mu l$ to thousands of microliters ($\mu l$), with a volume between 5 to 500 $\mu l$ being typical. The scanning system may be used for a variety of applications, such as, but not limited to, fluorescent PCR-based detection.

Likewise, although certain preferred embodiments employ trays with sample wells, the present invention is suitable for use with sample trays that do not include wells. The tray may include any type of sample holder that can maintain a sample in a fixed position on a tray. In certain embodiments, the sample trays may have a flat surface on which a sample of biological material is placed. The flat surface on which the sample is placed may be similar to a microscope slide for a sample. In this type of sample tray, a liquid may be dropped onto the tray at a plurality of positions, and then a film or cover positioned on the top surface of the tray over the samples. Alternately, a sample tray may include a porous material such as a frit on the top surface, instead of sample wells, for holding samples of biological material. Therefore, although the description refers to sample well trays throughout, it should be understood that the present invention is also suitable for sample trays that do not have sample wells.

Figure 7A:
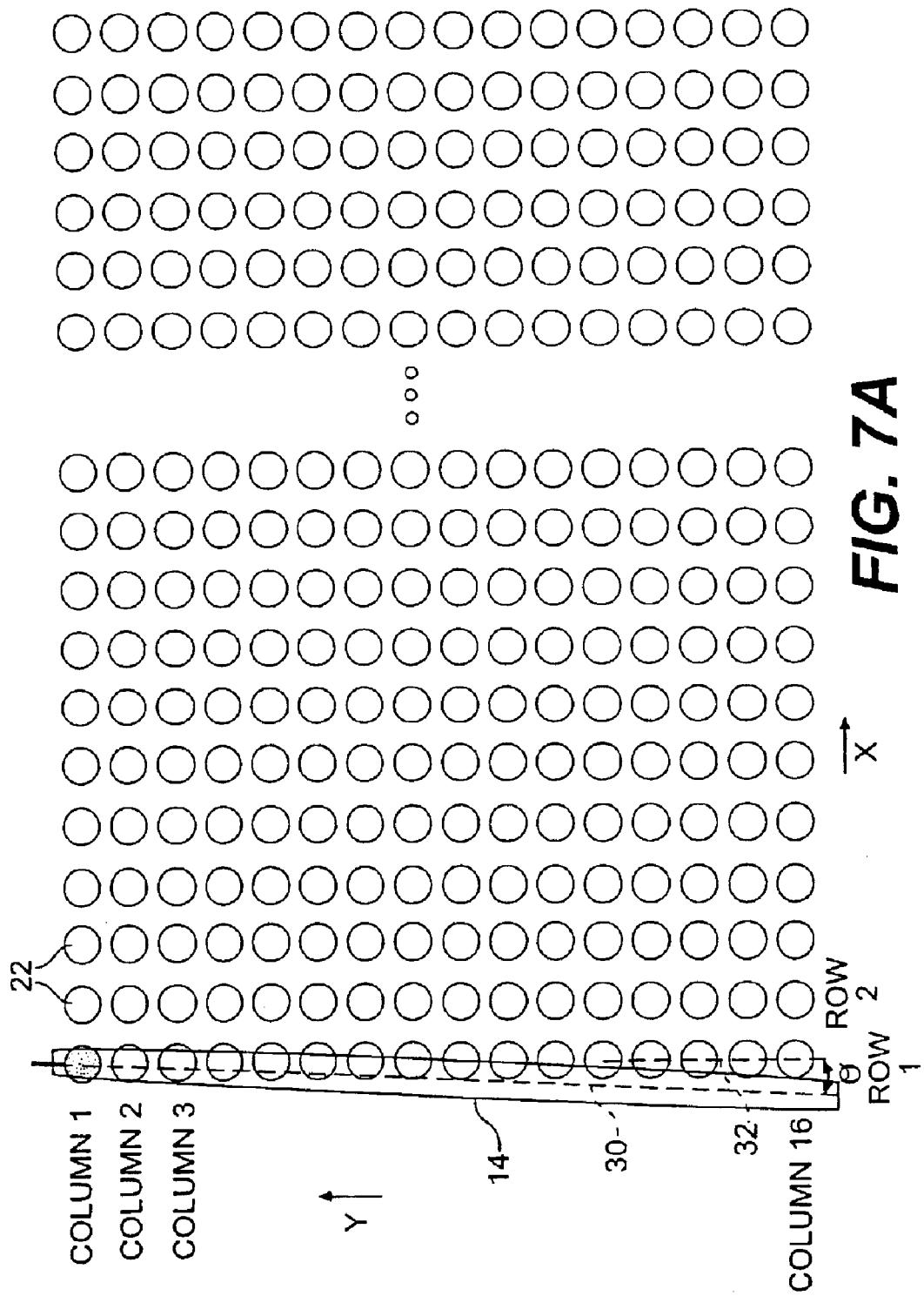
FIGS. 7A–7F illustrate a method of scanning the sample wells in a sample well tray according to the present invention.

For purposes of illustration only, the sample well tray described is a 384-well tray arranged in the sixteen by twenty-four array shown in FIG. 7A. For a 384-well sample tray with a conventional sixteen by twenty-four array, it is desirable to have sixteen well lenses in the well lens housing. Each well lens corresponds to a particular column of the sample well tray 24. For example, as shown in FIG. 7A, the first well lens of the row of well lenses corresponds to the first column of the sample well tray. Likewise, the second well lens of the row of well lenses corresponds to the second column of the sample well tray, and so forth.

In accordance with certain embodiments of the present invention, the row of well lenses are configured to be offset at an acute angle relative to a linear row of sample wells arranged in a first direction in a sample well tray. As embodied herein and shown in FIG. 7A, the well lens housing 14 (and row of well lenses 12) is arranged on a centerline 30 that passes through the center of each of the well lenses. The centerline 30 of the row of well lenses 12 is arranged to be offset at a predetermined angle $\theta$ relative to a centerline 32 passing through the first row of sample wells as shown in FIG. 7A. In certain embodiments, the angular offset $\theta$ between the row of well lenses and the row of sample wells allows the scanning system to operate by the desired method.

Figure 7B:
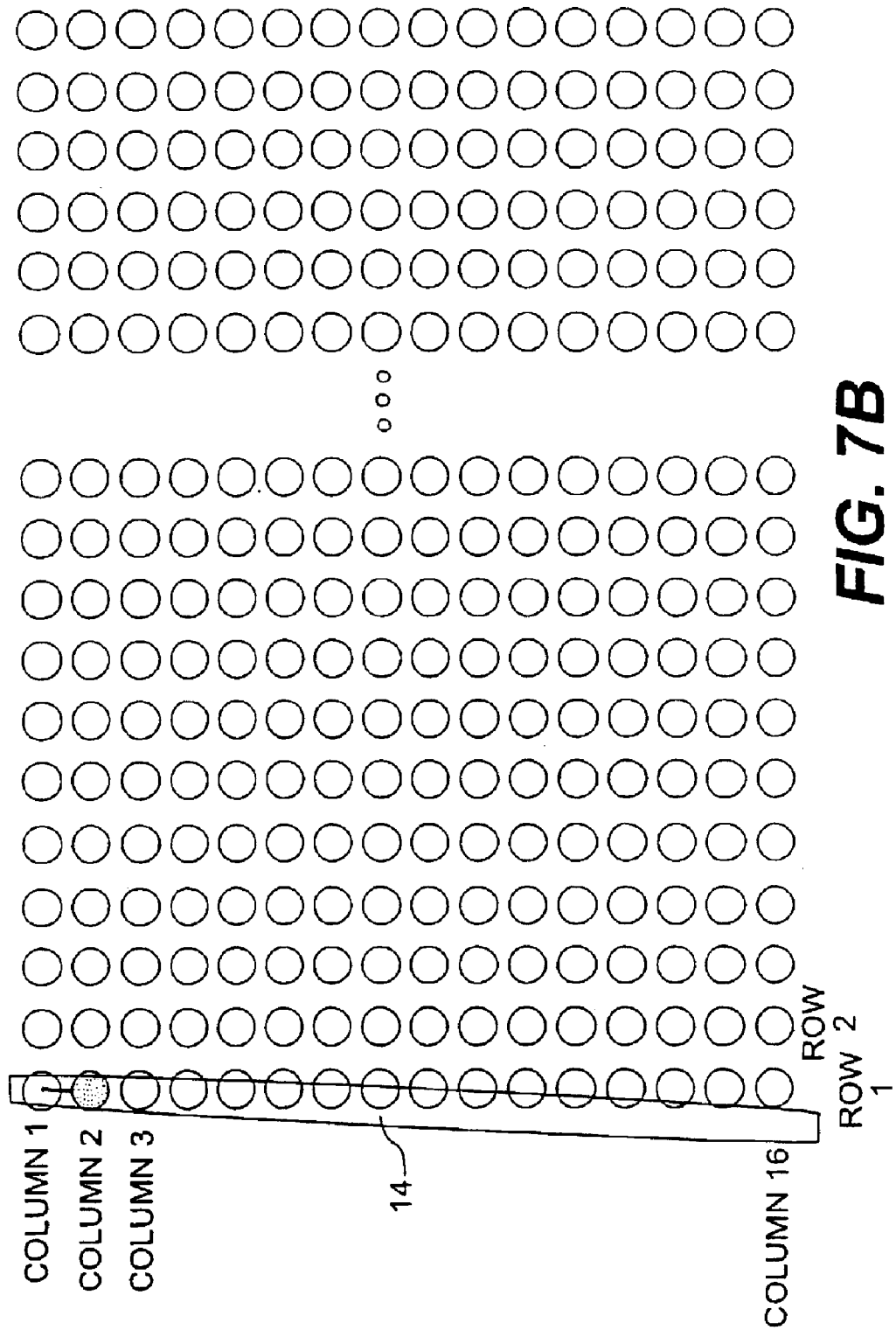

In view of the arrangement of the well lens housing and well lenses relative to the sample well tray, an excitation light can pass through the first well lens when the well lens is aligned with the first sample well (column 1) of the first row of the sample well tray, as shown in FIG. 7A. The first sample well is thereby illuminated, generating an emission light that is analyzed by an optical system. As the well lens housing continues to translate at a substantially uniform speed in the x-axis direction to the position shown in FIG. 7B, an excitation light is passed through a second well lens when the second well lens is aligned with the second sample well of the first row as shown in FIG. 7B. An excitation light direction mechanism according to certain embodiments of the present invention directs the excitation light from one well lens to another in a sequential manner. The excitation light should be directed to the respective well lens at the time at which the well lens is substantially aligned with an adjacent sample well. This process continues so that all of the sample wells in the first row are scanned, and then continues to the next row, thereby scanning all of the sample wells in the second row. This process continues until all of the sample wells are scanned.

In certain embodiments, the angle $\theta$ between the row of sample wells and the row of well lenses is selected as a function of the number of sample wells and the spacing between adjacent sample wells. In the configuration shown in FIG. 7A, the angle $\theta$ is selected to be between one and three degrees, preferably approximately two degrees. In certain embodiments, this is a suitable angle for a sample well tray having spacing of 4.5 mm and sixteen sample wells in each row. In certain embodiments, the angle is selected so that an entire row is scanned before any of the well lenses are aligned with the next row to be scanned. The value for the angle $\theta$ can vary for each specific design and is not limited by the range described above. For example, in a 96-well format with one particular design, the angle $\theta$ is selected to be approximately four degrees.

In accordance with certain embodiments of the present invention, the well lens housing may be translated relative to a stationary sample well tray by a linear actuator or other device. Alternately, the well lens housing may be stationary and the sample well tray translated relative to the stationary well lens housing. The operation and principles of the present invention typically are identical with either configuration. For purposes of illustration only, the present description will be directed toward the embodiments with a well lens housing being translated relative to a stationary sample well tray. In embodiments with a stationary sample well tray, the well lens housing is typically linearly translated in a plane substantially parallel to the top of the sample well tray. As shown for example in FIG. 2, the well lens housing 14 may be translated in a first direction (into the page in FIG. 2) relative to the sample well tray 24. In certain preferred embodiments, the well lens housing 14 is translated at a substantially uniform speed relative to the stationary sample well tray 24. As shown in FIGS. 7A–7F, the sample well tray translates along the sample well tray so that all twenty-four sample well rows may be scanned. According to certain embodiments of the present invention, the well lens housing translates at a uniform speed so that the scanning device does not undergo the accelerations associated with stopping and starting during an intermittent motion. Therefore, the well lens housing does not dwell over each individual sample well, but instead moves at a substantially constant speed. Preferably, the well lens housing moves at a sufficiently slow speed that the optical system is able to obtain an accurate analysis of each sample well. In certain examples where the angle $\theta$ is 2 degrees, the well lens housing is translated at a predetermined speed so that the well lens is aligned with the corresponding sample well for approximately 5 milliseconds. The alignment time is determined by $\theta$, which may be selected as desired to achieve optimal results. In certain embodiments where the sample concentration is low, the alignment time may be as much as 20 milliseconds. In certain embodiments where maximum sample throughput and speed are desired, the alignment time may be as low as 1 millisecond.

The well lens housing 14 and scanning system 10 may be translated by any suitable type of linear actuator, such as a motor driven carriage assembly. Alternately, as mentioned above, the sample well tray may be translated relative to a stationary well lens housing. In certain embodiments in which the well lens housing 14 translates relative to a stationary sample well tray, the well lens housing 14 may be positioned on a scanning carriage with a screw actuator for linearly translating the scanning carriage. The screw actuator is typically rotated by a motor or other device, and the scanning carriage may slide on one or more guide rods. Other types of linear actuators may also be suitable with the present invention.

In certain embodiments, the plurality of lenses may be joined together into an integral lens. In certain alternate embodiments, a single lens, such as a cylindrical lens, may be used instead of a plurality of well lenses. In such an arrangement, the single lens would be positioned at approximately the same location as the plurality of well lenses described above. The excitation light will be allowed to pass through the cylindrical lens to the sample well tray, and the excitation light will pass back through toward the optical detection system. The use of a single lens has an advantage of requiring less-precise timing for the excitation light to strike the respective sample well. However, in certain embodiments, a single lens may suffer from reduced optical quality compared to the multiple well lens configuration shown in the figures.

In accordance with certain embodiments of the present invention, the scanning system 10 includes an excitation light source 16 that generates an excitation light to illuminate the samples in the sample wells, as shown in FIG. 1. One or several excitation sources may be provided. In certain embodiments, excitation is provided to the sample by an Argon ion laser. Other types of conventional light sources may also be used. The excitation source is typically selected to emit excitation light at one or several wavelengths or wavelength ranges. In certain examples, a laser having a wavelength of 488 nm is used for generating the excitation light. The excitation light from excitation light source 16 may be directed to the well lenses by any suitable manner. In certain embodiments, the excitation light is directed to the well lenses by using one or mirrors to reflect the excitation light at the desired well lens. After the excitation light passes through the well lens into an aligned sample well, the sample in the sample well is illuminated, thereby emitting an emission light. The emission light can then be detected by an optical system. The excitation light is then directed to another well lens so that a second sample well may be illuminated.

Figure 5:
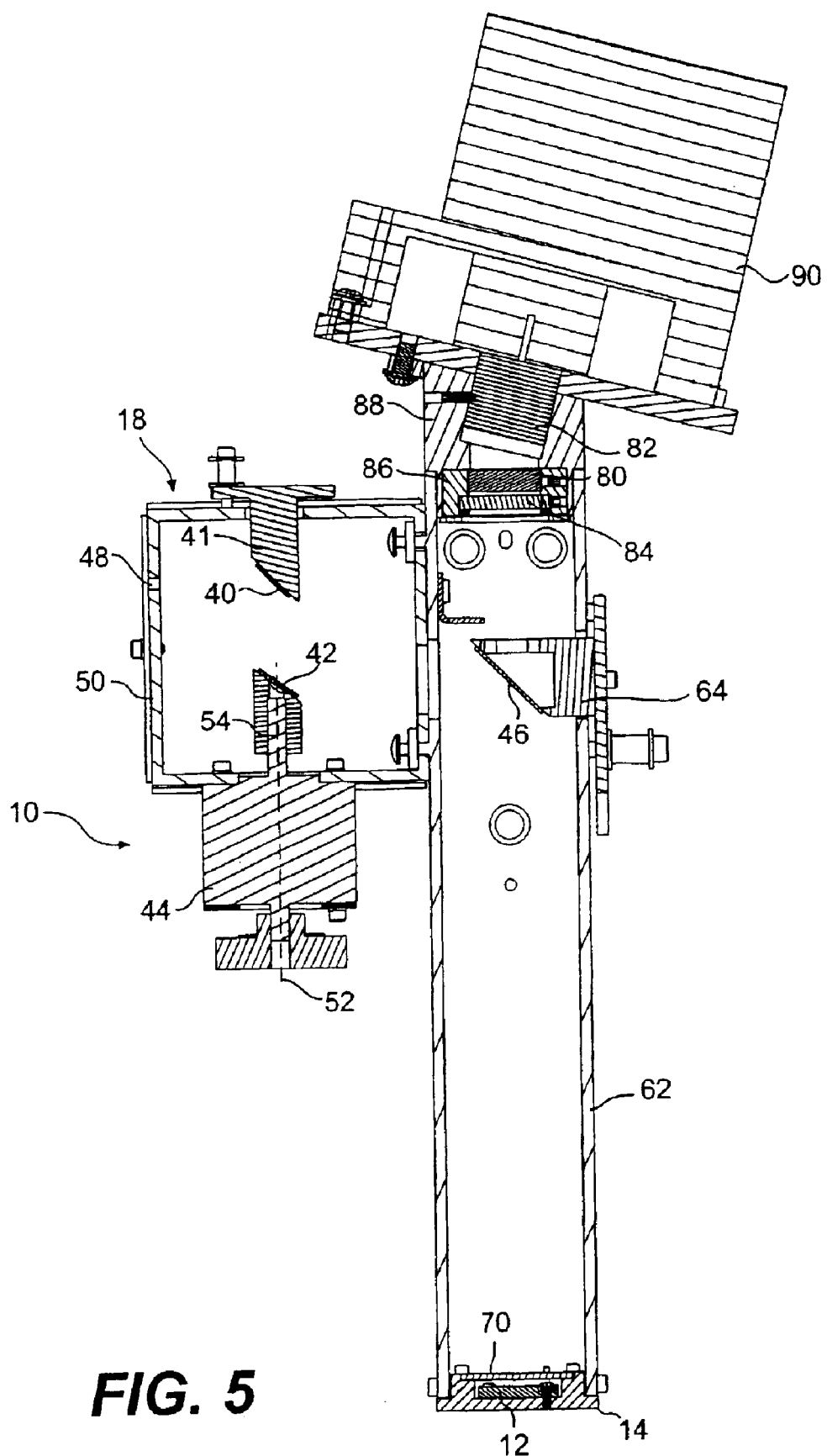
FIG. 5 is a side view of a system according to certain embodiments of the present invention.
Figure 6:
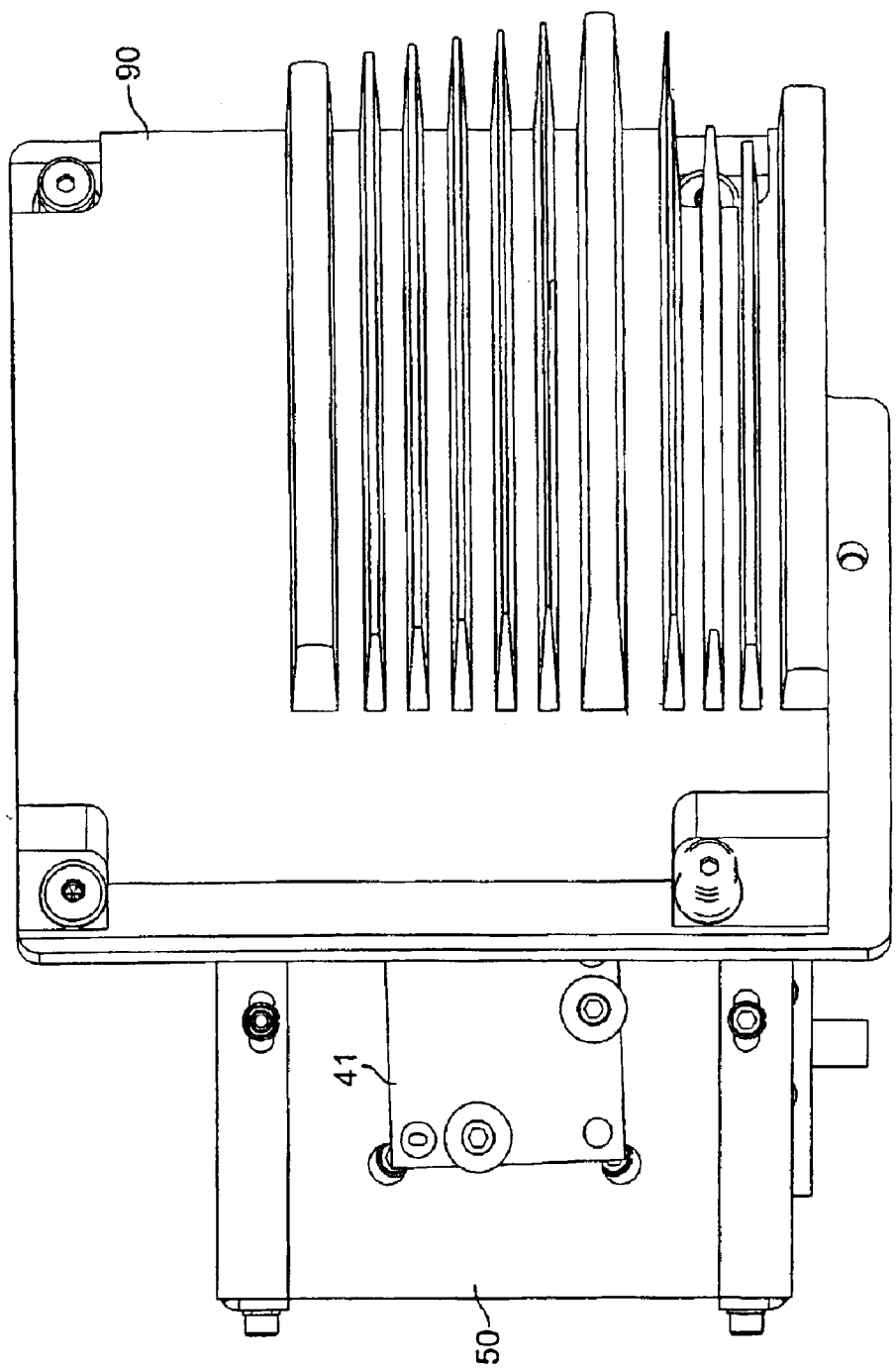
FIG. 6 is a top view of the system of FIG. 5.

In accordance with certain embodiments of the present invention, the scanning system 10 includes an excitation light direction mechanism 18 for directing the excitation light to a single well lens 12 at a time. According to certain embodiments shown in FIGS. 1–6, the excitation light direction mechanism 18 includes a stationary mirror 40, a rotating mirror 42, a motor 44 for rotating the rotating mirror 42, and a beam splitter 46. The excitation light direction mechanism is configured so that the excitation light may be intermittently directed at each of the well lenses 12 in a sequential manner. As shown in FIG. 1 and FIG. 5, the stationary mirror 40 reflects the excitation light from the laser 16 to the rotating mirror 42. In certain embodiments, the excitation light passes through an aperture 48 in the mirror housing 50 as it travels between the laser 16 and the stationary mirror 40, as shown in FIG. 5. The stationary mirror 40 may be mounted to the mirror housing 50 in any suitable manner and at any suitable angle. In certain embodiments, the stationary mirror is mounted on the mirror housing by an adjustable mount 41. In other embodiments, the stationary mirror may be eliminated and the laser 16 may be positioned so that it directs the excitation light directly onto the rotating mirror 42.

According to certain embodiments shown in FIGS. 1–5, the rotating mirror 42 is positioned at an angle to the rotational axis 52 of a scan motor 44. The scan motor rotates the rotating mirror about the rotational axis 42. The scan motor 44 is mounted to a bottom of the mirror housing 50 in any suitable manner. The rotating mirror is attached to an output shaft 54 of the scan motor 44 by any suitable manner. In the example shown in FIG. 5, the rotating mirror 42 is positioned on a sleeve 56 that is rotatably fixed to the output shaft 54 of the scan motor. As shown in FIG. 1, the surface of the rotating mirror may be positioned at an angle of forty-five degrees to the rotational axis 52 of the scan motor 44. With the surface of the rotating mirror 42 arranged at a forty-five degree angle, the excitation light beam reflects at an angle of ninety degrees to the rotational axis 52, as shown by beam 60 in FIG. 1. The excitation light beam 60 will maintain the ninety degree angle relative to the incoming beam for every rotational position of the rotating mirror. However, as the rotating mirror is rotated about the rotational axis 52, the reflected excitation beam 60 will move about the rotational axis 52.

In certain embodiment, the present invention is configured so that the scan motor rotates to sixteen discrete angular positions, so that each discrete angular position corresponds to a particular well lens. In particular, the motor is a stepper motor that has a limited range of rotation. For example, in one embodiment, a fifteen degree range of rotation will cause the excitation light to travel from the first to the sixteenth well lens in a given row. The rotating mirror 42 starts at a first angular position corresponding to the first lens, pauses at this position for a predetermined length of time so that the sample well aligned with the first well lens may be scanned, and then rotates to a second angular position for a predetermined period, and so forth until the excitation light has been directed at all sixteen well lenses. After the sixteenth well lens, the motor rotates the mirror back to the first position corresponding to the first well lens. In certain embodiments, the timing of the rotation of the scan motor is coordinated with the speed of translation of the well housing so that the excitation light passes through the correct well lens at the desired time. In other words, the excitation light is directed at the first well position when the first well lens is properly positioned above the first sample well, and the excitation light is directed at the second well position when the second well lens is properly positioned above the second sample well, and so forth.

According to certain embodiments, the scanning system includes a beam splitter 46 that not only reflects the reflected excitation light 60 to the well lens, but also allows the returning emission light to pass through it. As shown in FIG. 5, a beamsplitter can be positioned in a scan housing 62. The beam splitter 46 may be mounted in the scan housing by any suitable method and at any suitable angle. In the example shown in FIG. 5, the beam splitter is attached to the scan housing by an adjustable two-position mount 64. In certain embodiments, the beam splitter is a dielectric beam splitter that reflects the incoming excitation light, but permits the emission light to pass through it to the optical detection system 20.

In the embodiments shown in FIGS. 1–5, the reflecting surface of the beam splitter 46 is arranged at a forty-five degree angle to the side of the scan housing 62. The beam splitter reflects the incoming reflected excitation light 60 to the corresponding well lens 12. As shown in FIG. 2, depending on the angle of rotation of the scan motor 44, the reflected light 60 will strike a different position on the beam splitter. The excitation light for each of the positions of the beam splitter corresponds to a different well lens of the well lens housing, as shown in FIG. 2. For example, the position marked $x_1$ in FIG. 2 corresponds to the position at which the reflected excitation light 60 will strike the beam splitter in order to be reflected to the first well lens position and the first sample well. Likewise, the position marked $x_{16}$ corresponds to the position at which the reflected excitation light 60 will strike the beam splitter in order to be reflected to the sixteenth well lens position and the sixteen sample well of the row. As can be seen in FIG. 2, the other positions corresponding to the second through fifteenth well lens positions are located between these two points. Each one of these sixteen positions on the beam splitter corresponds to a discrete angular position of the rotating mirror.

In certain embodiments of the present invention, a lens such as fresnel lens 70 is positioned between the beam splitter 46 and the well lenses 12. The fresnel lens 70 is preferably configured to change the angle of each incoming excitation light so that the excitation light is centered in the appropriate well lens 12 and sample well 22. The fresnel lens provides a telecentric viewing of the sample wells so that the well lens may focus the excitation light to a small spot on the sample of the sample wells. In certain examples, the fresnel lens has a focal length of 254 mm. The focal length of the fresnel lens may be varied depending on the specific configuration of the device. The fresnel lens 70 may be mounted in the system, e.g., to the well lens housing 14, in any suitable manner, such as by bolts or other fasteners.

Other types of lenses beside fresnel lenses may be positioned between the beam splitter 46 and the well lenses 12.

Instead of a fresnel lens, a standard telecentric objective may be used. A telecentric lens is typically more expensive but may result in a better quality image. Other types of lenses are also suitable.

An aperture (not shown) may also be provided between the fresnel lens and the well lens to reduce stray light and reduce cross talk between the sample wells according to certain embodiments. The aperture may also be used to set the resolution of the optical detection system 20 according to certain embodiments. The apertures may be of a variety of geometric shapes including, but not limited to, round, rectangular, and square.

After passing through the fresnel lens, the excitation light passes through a well lens 12 and is focused on the sample in the adjacent sample well. The sample preferably is located at approximately the focal distance from the well lens so that the excitation light will be directed onto the sample. The light emitted from the sample (emission light) after being struck with the excitation light will be collected by the well lens 12. The emission light from the sample that is collected by the well lens 12 is then directed back to the fresnel lens 70 toward the beam splitter 46. The beam splitter is configured so that the emission light from the sample well is permitted to pass through to the optical detection system 20.

In accordance with certain embodiments of the present invention, an optical detection system 20 is provided for analyzing emission light from each sample well that passes through the beam splitter 46. In accordance with certain embodiments of the present invention, the optical system includes a light separating element such as a light dispersing element. A light dispersing element can be any element that spectrally separates incoming light into its spectral components. For example, incoming light can be deflected at an angle roughly proportional to the wavelength of the light. Thus, different wavelengths are separated. Suitable light dispersing elements include a transmission grating, a reflective grating, or a prism. In a transmission grating, light passes through the grating and is spectrally dispersed, whereas, in a reflective grating, incoming light is reflected off of the grating surface at an angle, without passing through the grating surface. In other embodiments, the light separating element may be a beamsplitter or filter such as a dichroic filter that is used to analyze a single wavelength without spectrally dispersing the incoming light. In a configuration with a single wavelength light processing element, the optical detection device is limited to analyzing a single wavelength, thereby one or more light detectors each having a single detection element may be provided.

For purposes of illustration only, in embodiments where the light separating element spectrally disperses the incoming light, the light dispersing element will be described as a transmission grating 80, such as shown in FIGS. 1–5. Typically, a grating will have hundreds or thousands of grooves per mm. In certain particular embodiments, the grating groove density may range from about 100 grooves/mm to about 1,200 grooves/mm. In certain examples, the grating groove density is approximately 424 grooves/mm.

The light dispersing element spreads the light spectrally in a direction substantially perpendicular to spectral channels on the light detection device. This configuration creates a two-dimensional image on the light detection device after the light passes through a lens element 82. The lens element may be any type of suitable lens, such as a camera lens, which focuses the light onto a light detection device. In certain embodiments, the lens element 82 is a multi-element camera lens with a focal length of 24.5 mm and an aperture speed of 1.6.

The optical system may further include one or more blocking filters to prevent significant amounts of excitation light or other background light (from other sources) from reaching the light detection device. In certain embodiments, one or more blocking filters, such as long-pass filters, may be provided in the optical path of the emission light. FIGS. 1–5 show an excitation blocking filter 84 positioned between the beam splitter 46 and the transmission grating 80. The filter 84 may be configured to allow any suitable range of wavelengths to pass through it and to block wavelengths outside that range from passing through it. In certain examples, the blocking filter permits light having a range of approximately 510 to 650 nm to be transmitted through it. Other types of filters may also be used throughout the scanning system. In the example shown in FIG. 5, the blocking filter 84 and transmission grating 80 are arranged in a housing 86 at the top of the scan housing 62. The lens element 82 is positioned in a lens housing 88 adjacent the housing 86 as shown in FIG. 5.

Preferably, the optical detection system further includes a light detection device 90 for analyzing light from a sample for its spectral components. In certain embodiments, the light detection device comprises a multi-element photodetector. Exemplary multi-element photodetectors may include, for example, charge-coupled devices (CCDs), diode arrays, photo-multiplier tube arrays, charge-injection devices (CIDs), CMOS detectors, and avalanche photodiodes. In certain embodiments, the light detection device may be a single element detector. With a single element detector, a single sample well may be read at a time. A single element detector may be used in combination with a filter wheel to take a reading for a single sample well at a time. With a filter wheel, the sample well tray typically is scanned a large number of times, each time with a different filter. Alternately, other types of single dimensional detectors are one-dimensional line scan CCDs, and single photomultiplier tubes, where the single dimension could be used for either spatial or spectral separation.

According to certain embodiments of the present invention used with a light dispersing element, a CCD is typically used to view all of the wells of a row. In the embodiment described above, the CCD obtains a thirty-two point spectrum for each of the sixteen wells of a row. The spectrum is formed on a surface 90 of the CCD camera and analyzed for its spectral components. In certain embodiments, the CCD element is thermally cooled and has an array of 64 by 512 pixels, and a resolution of 0.027 mm. In a typical operation, the spectrum for each sample is read after the entire row of wells has been scanned.

Methods of scanning a sample well tray having a plurality of samples positioned in sample wells are apparent from the description of the various embodiments of the scanning system above. The methods include generating an excitation light with an excitation light source. As discussed for certain examples, a laser 16 may generate an excitation light. The method further includes directing the excitation light to a first well lens in a row of well lenses, as shown, for example in FIG. 7A.

In certain examples, directing the excitation light to the well lens includes reflecting the excitation light against a mirror, and rotating the mirror to discrete positions so that the reflected excitation light is directed at a corresponding well lens. In certain embodiments, the excitation light is directed against a rotating mirror 42 that is sequentially rotated to sixteen discrete angular positions about a rotational axis 52. The rotating mirror 42 is angled relative to the rotational axis so that each of the discrete angular positions corresponds to a particular well lens 12 of the well lens housing. In certain embodiments, the light from the rotating mirror 42 is reflected off of a beam splitter 46 toward a corresponding well lens. In certain embodiments, the row of well lenses is angularly offset relative to an adjacent row of sample wells.

The method further includes illuminating a sample in a first sample well of the row of sample wells positioned adjacent the row of well lenses with the excitation light to generate an emission light. The sample is caused to fluoresce by the excitation source so that it emits an emission light.

The method further includes optically detecting the optical characteristics of the emission light from the sample well. In certain examples, the emission light from the sample well passes through the same sample well as the excitation light had previously passed through on its way to the sample well. The emission light is directed toward an optical detection system, such as optical detection system 20. In certain embodiments, the step of optically detecting the spectral characteristics of the emission light includes spectrally dispersing the emission light with a light dispersing element, such as a transmission grating, which spectrally disperses the emission light. The dispersed light from the light dispersing element is then directed onto a light detection device by a lens element. The light detection device, for example, a charge coupled device (CCD) detects the spectral characteristics of the emission light. The spectral characteristics may then be analyzed by any methods or devices. In certain embodiments, the light is not spectrally dispersed but is separated by a light separating element such as a filter.

After scanning a first sample well, according to certain embodiments, the method further includes directing the excitation light to a second well lens positioned adjacent the first well lens of the row of well lenses. The excitation light illuminates a sample in a second sample well of the row of sample wells with the excitation light to generate another emission light. The sample of the second sample well is caused to fluoresce by the excitation source so that it emits an emission light. In certain embodiments, the rotating mirror 42 rotates to a second angular position so that the excitation light is directed to the second well lens, as shown for example in FIG. 7B. At the time the excitation light is directed at the second well lens, the row of well lenses has translated in a direction perpendicular to the row of sample wells at a substantially uniform speed (in the "x" direction as labeled in FIG. 7A). At the position shown in FIG. 7B, the second well lens is aligned with a second well of the first row of sample wells.

The spectral characteristics of the emission light from the second sample well may then be optically detected in the same manner as described above for the first sample well. Throughout the above method, the row of well lenses and sample tray are moved relative to one another. In certain configurations, the row of well lenses linear translates relative to a stationary sample tray. In certain other configurations, the sample tray linearly translates relative to a stationary row of well lenses.

Figure 7F:
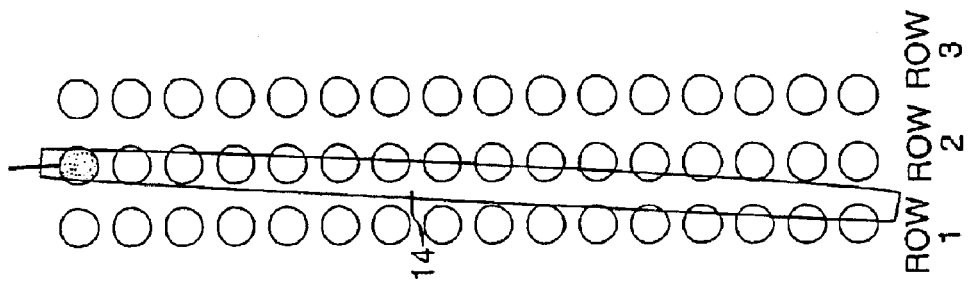
Figure 7E:
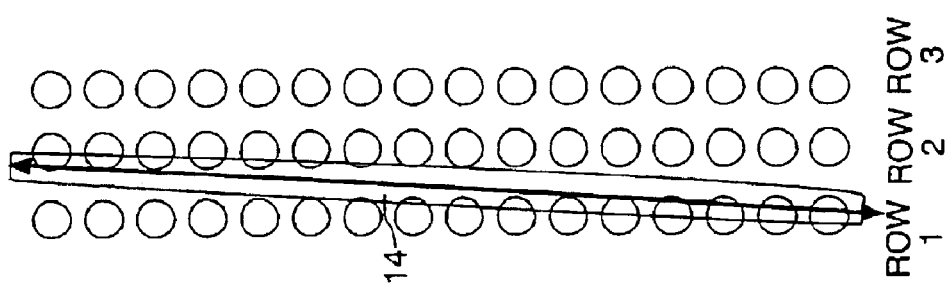
Figure 7D:
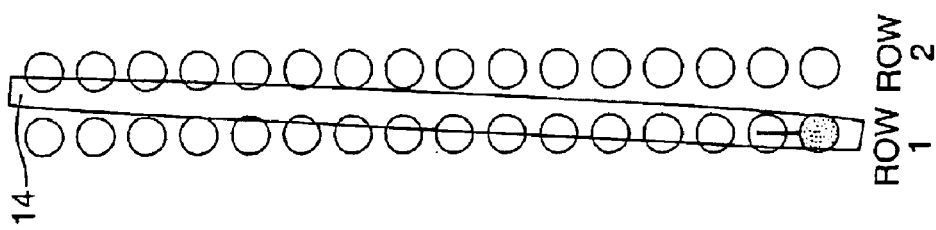
Figure 7C:
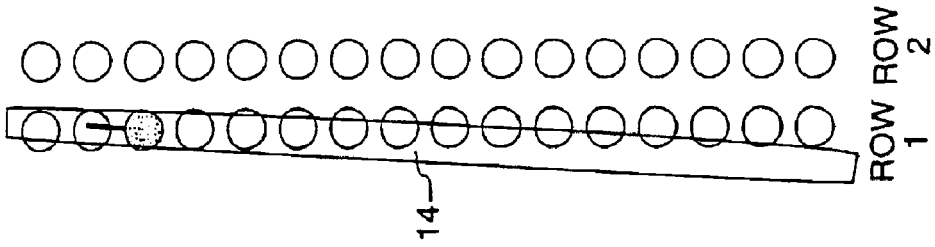

The method may further include optically detecting the spectral characteristics of the emission light from the remaining sample wells in the row as the well lenses continue to translate in the perpendicular direction. After the last sample well of the row (see FIG. 7D) has been optically detected, the light detection device takes a reading of the spectral characteristics of the entire row. The well housing 14 continues to translate in the x-direction (see FIG. 7E) so that the first well lens of the row of well lenses is eventually aligned with the first sample well of the second row of sample wells, as shown in FIG. 7F. At this position, the excitation light direction mechanism directs the excitation light to the first well lens so that the aligned sample well may be illuminated and optically detected. The procedure continues until the entire sample tray has been scanned.

The method may also comprise other procedures such as blocking a portion of light having a wavelength lower than a predetermined wavelength using a blocking filter. Other methods suitable with the scanning system described above may also be used.

It will be apparent to those skilled in the art that various modifications and variations can be made in the scanning system, methods of scanning a sample well tray, use of the system of the present invention, and in construction of this system, without departing from the scope or spirit of the invention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims. All documents cited herein are incorporated by reference for any purpose.

What is claimed is:

1. A system for scanning a plurality of samples, comprising:
    a lens housing comprising a plurality of lenses positioned in a linear row, each lens configured to direct excitation light to and collect fluorescent light from a single aligned sample at a time; and
    a rotating mirror to direct the excitation light to a single lens at a time, wherein the single lens is aligned to the single sample.

2. The system of claim 1, further comprising a light detection device for analyzing the fluorescent light collected from the sample.

3. The system of claim 2, further comprising a transmission grating between the lens housing and the light detection device.

4. The system of claim 3, further comprising a filter between the lens housing and the light detection device.

5. The system of claim 4, wherein the light detection device is a charge-couple device.

6. The system of claim 5, wherein the charge-couple device is configured to analyze the spectrum for each of the sample holders, the spectrum for each of the sample holder being spatially separated on the charge-coupled device from the spectrum for the adjacent sample holder.

7. A system for analyzing a plurality of samples, comprising:
    several excitation sources for generating excitation light;
    a lens housing comprising a plurality of lenses, each lens configured to direct excitation light to and collect fluorescent light from the plurality of samples, wherein each lens is aligned to each sample; and
    a rotating mirror to direct the excitation light to a single lens at a time, wherein the single lens is aligned to a single sample.

8. The system of claim 7, further comprising a light detection device for analyzing the fluorescent light collected.

9. The system of claim 8, wherein the light detection device is a multi-element photodetector.

10. The system of claim 8, wherein the light detection device is a single-element photodetector.

11. A method of scanning a plurality of samples to detect fluorescence, comprising:
- providing excitation light from several excitation light sources;
- translating a linear row of lenses to direct excitation light to and collect fluorescent light from a single sample holder at a time;
- rotating a mirror to direct the excitation light to a single lens at a time, wherein the single lens is aligned to a single sample; and
- detecting the fluorescent light.

12. The method of claim 11, wherein the translating comprises linear movement at substantially uniform speed.

13. A method of scanning a plurality of samples to detect fluorescence, comprising:
- providing excitation light from an excitation light source;
- providing a lens housing comprising a linear row of lenses;
- providing a sample tray comprising the plurality of samples;
- translating a row of lenses to direct excitation light to and collect fluorescent light from a single sample holder at a time;
- rotating a mirror to direct the excitation light to a single lens at a time; and
- detecting the fluorescent light.

14. The method of claim 13, wherein the translating comprises linear movement at substantially uniform speed.

15. A method of detecting fluorescence from a plurality of samples, comprising:
- providing excitation light from several excitation light sources;
- providing a lens housing comprising a plurality of lenses;
- providing a sample tray comprising a plurality of samples;
- positioning the lens housing to direct excitation light to and collect fluorescent light from a single sample holder at a time;
- rotating a mirror to direct the excitation light to a single lens at a time, wherein the single lens is aligned to a single sample and
- detecting the fluorescent light.

16. The method of claim 15, wherein the detecting comprises reading a single sample well on a single element detector.

17. A system for detecting fluorescent light from a plurality of samples, comprising:
- several excitation sources for generating excitation light; and
- a lens housing comprising a plurality of lenses, each lens configured to direct excitation light to and collect fluorescent light from a plurality of samples, wherein each lens is aligned to each sample;
- a rotating mirror to direct the excitation light to a single lens at a time, wherein the single lens is aligned to a single sample;
- a light detection device for analyzing the fluorescent light collected; and
- apertures between the plurality of lenses and the light detection device to reduce cross-talk between samples.

18. The system of claim 17, wherein the light detection device is a multi-element photodetector.

19. The system of claim 17, wherein the light detection device is a single-element photodetector.

* * * * *